(12) United States Patent
Korteweg et al.

(10) Patent No.: US 6,183,436 B1
(45) Date of Patent: Feb. 6, 2001

(54) ARTICLE FOR PACKING BODY CAVITIES

(75) Inventors: Wayne Korteweg, Ledyard; George P. Korteweg, Mystic, both of CT (US)

(73) Assignee: Ultracell Medical Technologies of Connecticut, Inc, North Stonington, CT (US)

( * ) Notice: Under 35 U.S.C. 154(b), the term of this patent shall be extended for 0 days.

(21) Appl. No.: 09/151,870

(22) Filed: Sep. 11, 1998

(51) Int. Cl.⁷ .................................................. A61M 29/00
(52) U.S. Cl. ...................... 604/96; 604/358; 604/385.18; 424/431; 28/118; 28/120
(58) Field of Search ................................ 604/1, 2, 3, 904; 604/383, 96, 385.15; 128/285; 424/431; 28/118, 120

(56) References Cited

U.S. PATENT DOCUMENTS

| | | |
|---|---|---|
| 4,030,504 | 6/1977 | Doyle . |
| 4,341,214 * | 7/1982 | Fries et al. ............................ 128/285 |
| 4,883,465 * | 11/1989 | Brennan .................................. 604/96 |
| 4,925,453 | 5/1990 | Kanankeril . |
| 5,336,163 | 8/1994 | Demane et al. . |
| 5,466,231 | 11/1995 | Cercone et al. . |
| 5,556,391 | 9/1996 | Cercone et al. . |
| 5,584,827 | 12/1996 | Korteweg et al. . |

OTHER PUBLICATIONS

P. 318—Week Catologue.

* cited by examiner

Primary Examiner—John G. Weiss
Assistant Examiner—Michele Kidwell
(74) Attorney, Agent, or Firm—Ira S. Dorman

(57) ABSTRACT

An article for packing body cavities comprises a protective sheath of supple, smooth, polymeric film, containing an absorbent sponge or like tampon component. The sheath facilitates insertion and removal of the article by minimizing tissue attachment, adherence, abrasion, and desiccation of the tampon.

21 Claims, 2 Drawing Sheets

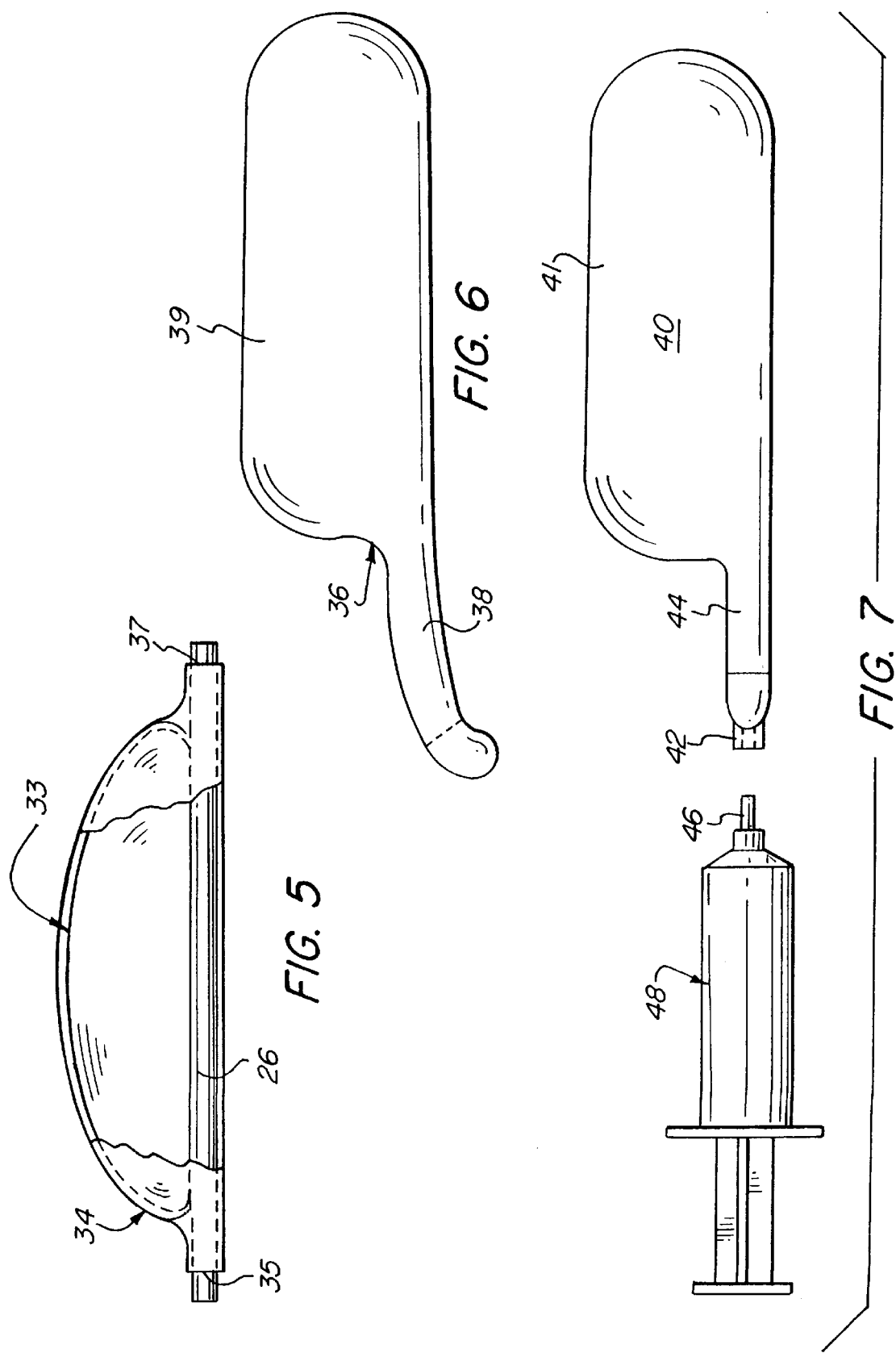

ARTICLE FOR PACKING BODY CAVITIES

BACKGROUND OF THE INVENTION

This invention relates to an article for packing body cavities, comprised of a tampon and a containing cover or sheath.

In U.S. Pat. No. 1,732,697, Ryan discloses a medicated, compressed sponge that is adapted for insertion into the nose and that swells into contact with the irregular surface portions of the nasal cavity, when moistened. Similarly, Steven U.S. Pat. No. 2,179,964, Kriwkowitsch U.S. Pat. No. 3,049,125, Gottschalk U.S. Pat. No. 3,570,494, Doyle U.S. Pat. Nos. 4,030,504, 4,646,739, and Des. 287,880, Rangaswamy U.S. Pat. No. 4,568,326, Brennan U.S. Pat. No. 4,950,280, DeMane et al. U.S. Pat. No. 5,336,163, Korteweg et al. U.S. Pat. No. 5,584,827, and Sweden patent No. 220,978 provide nasal hemostats and the like. A commercial product, sold under the GARDLOK designation, consists of a monoaxially compressed sponge tampon, which is intended for insertion into a supplied finger cot. Medical, catamenial, and like devices are disclosed in the following representative patents: Gearon U.S. Pat. No. 1,537,992, Munro U.S. Pat. No. 2,110,962, Robell U.S. Pat. No. 2,499,414, McLaughlin U.S. Pat. No. 2,739,593, Maro et al. U.S. Pat. No. 3,084,689, Penska U.S. Pat. No. 3,306,294, Crockford U.S. Pat. No. 3,369,544, Burnhill U.S. Pat. No. 3,762,414, Davis et al. U.S. Pat No. 3,791,385, Rosenblatt U.S. Pat. No. 4,098,728, Hirschman U.S. Pat. No. 4,175,561, Cercone et al. U.S. Pat No. 5,466,231, Cercone et al. U.S. Pat. No. 5,556,391, Canada Pat. No. 550,047, and France Pat. No. 718,042.

Efficient hemostasis, such as after septal, sinus, or rhinoplastic surgery, or to abate nasal hemorrhage, requires the application of gentle pressure to ruptured major arteries and blood vessels over substantially all parts of the nasal cavity. Moreover, it is highly desirable that there be no (or at most minimal) adherence or attachment of the hemostatic device to the adjacent tissue, resulting from ingrowth of the tissue or other mechanisms, so as to facilitate removal without undue discomfort to the patient or injury to the site of healing. It is particularly desirable that desiccation, with the accompanying stiffening and hardening of the sponge material that occurs, be avoided so as to again facilitate withdrawal with minimal pain and injury.

It is not believed that the devices provided heretofore function entirely adequately in either or both of the foregoing respects, or in other respects discussed hereinbelow.

SUMMARY OF THE INVENTION

Accordingly, it is the broad object of the present invention to provide a novel body cavity-packing article, and in particular a nasal cavity-packing article, comprised of a dry, expansible, tampon component that is substantially isolated from contact with body tissue and is protected against desiccation.

A more specific object is to provide such an article that is effective to apply gentle pressure to substantially all parts of the packed cavity, including relatively inaccessible openings and recesses thereof.

Related objects of the invention are to provide such an article which avoids undue pressure in or overpacking of the cavity, which is readily and comfortably inserted, worn, and removed, and which is of relatively simple and inexpensive manufacture.

It has now been found that certain of the foregoing and related objects of the intention are attained by the provision of an article for packing a body cavity, comprising a sheath of smooth, supple, polymeric film (generally of fluid-impermeable character); a tampon continued within the sheath; and a retrieval element. The sheath has a containment portion with a closed posterior end and with structure defining an entrance aperture at its anterior end, and with perforations advantageously being formed along length of the containment portion between the anterior and posterior ends. The entrance aperture structure lies substantially in a transverse plane and has a peripheral dimension that is substantially smaller than the peripheral dimension of any cross sectional element, taken along the length of the containment portion and lying in a plane parallel to the plane of the aperture structure. The tampon is of elongate form and is loosely disposed within the containment portion of the sheath; it is comprised of an absorbent material that is expansible when wetted from a dry, compressed state, and is compressed in two directions that are perpendicular to one another as well as to the longitudinal axis of the tampon. The retrieval element extends from adjacent the anterior end of the sheath, and is operatively attached for effecting withdrawal of the tampon from the containing body cavity.

In certain embodiments the sheath will include an anterior portion that extends outwardly from the anterior end, in a direction away from the containment portion. Such an anterior portion may serve as both an anterior end closure and also as a retrieval element, and it will desirably be elongate and of reduced transverse cross section (usually having a peripheral dimension the same as that of the entrance aperture structure, taken in planes parallel to the plane thereof). The sleeve will advantageously be configured to correspond generally to the shape of the body cavity in which the article is to be contained. The film from which the sheath is made will preferably have a thickness of about 0.5 to 3 mils and a Shore A Durometer value in the range of 20 to 60 (and preferably 30 to 45); in most instances it will comprise a biocompatible polymer, such as a medical or surgical grade of latex, silicone, polyolef in, polyurethane, or polyester.

The absorbent material comprising the tampon of the article will normally be an open-cell sponge, such as of cellulose, polyvinyl alcohol, polyvinyl acetal or formal, polyurethane, or other suitable (usually hydrophilic) material; combinations of different sponge materials may be employed so as to impart variations in composition, density, porosity, and the like. In compressed form the tampon will desirably have a substantially rectangular cross section, taken in planes transverse to its length dimension. The sheath will advantageously be dimensioned and configured to contain the fully expanded tampon without significant distortion of one component by the other, albeit that in some instances differential compression by the sheath may beneficially provide areas of the sponge having different effective densities.

In certain preferred embodiments the article will additionally include a hollow tube extending between the anterior and posterior ends of the sheath containment portion, and usually through the tampon as well, to provide an airway through the article. At least the posterior end of the sheath will, in such instances, sealingly engage the tube, and an aperture may be provided thereat to receive the corresponding end portion of the tube. Inherent elasticity of the polymeric film may be relied upon to cause the surrounding structure to grip the tube circumferentially, and a similar arrangement may be present at the anterior end.

BRIEF DESCRIPTIONS OF THE DRAWING

FIG. 5 is another similar view, showing an embodiment in which the air tube is disposed exteriorly of the tampon;

FIG. 6 is a plan view showing another form of the sheath of which the articles of the invention are comprised; and FIG. 7 is an exploded plan view showing a syringe and article embodying the invention, having fittings for interengagement with one another.

DETAILED DESCRIPTION OF THE PREFERRED ILLUSTRATED EMBODIMENTS

Figure 1:
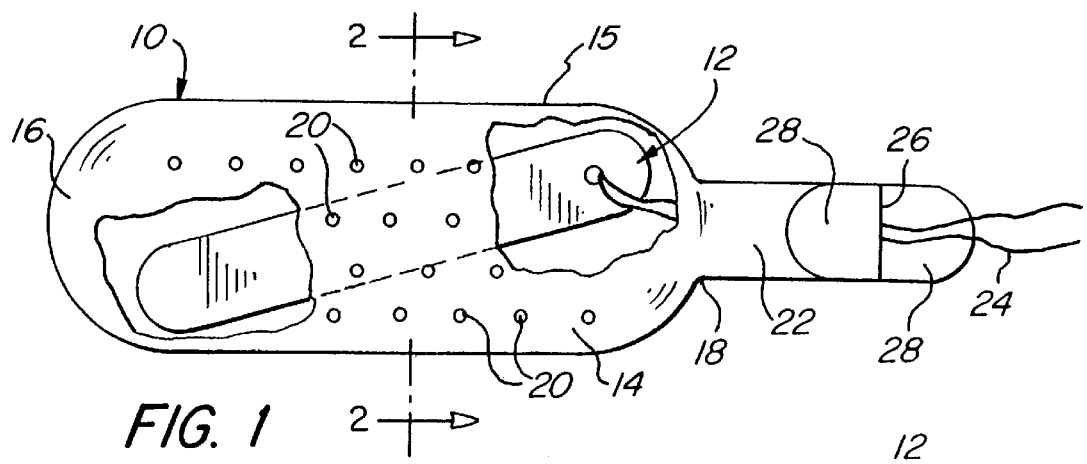
FIG. 1 is a plan view of an article embodying the present invention, with portions of the sheath component broken away to expose the compressed, dry tampon component contained therewithin.
Figure 2:
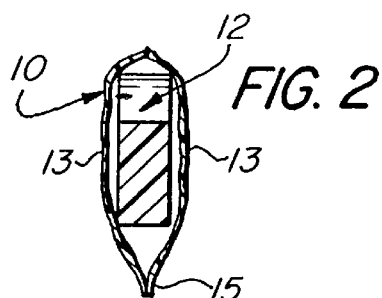
FIG. 2 is a sectional view of the article of FIG. 1, taken along line 2—2 thereof.

Turning initially to FIGS. 1 and 2 of the drawings, therein illustrated is an article embodying the present invention and consisting of a sheath, generally designated by the numeral 10, and a tampon, generally designated by the numeral 12. The sheath 10 is made from a smooth, supple, fluid-impermeable polymeric film, two layers of which are superimposed as sidewalls 13 and heat-sealed peripherally at 15. It consists of a containment portion 14 having a closed posterior end 16, anterior end structure at 18 defining an entrance opening, and elongate regions of the opposite sidewalls 13 perforated with small apertures 20. The film layers are so configured as to also provide a neck portion 22 extending from the anterior end of the containment portion 14.

The tampon component 12 comprises an open-cell sponge. As depicted in FIGS. 1 and 2, the sponge is in a dry, compressed state, and has a generally rectangular cross-sectional configuration (seen in FIG. 2), resulting from its compression in two directions that are perpendicular to one another as well as to the longitudinal axis of the tampon. As will be appreciated, the tampon 12 is introduced into the containment portion 14 of the sheath 10 through the neck portion 22 and the entrance aperture structure 18, the dimensions of which are sufficient (and preferably, just so) to enable ready insertion. As will also be appreciated, the biaxial compression of the tampon reduces it to small dimensions, which in turn permits the neck portion 22 and aperture structure 18 to be of correspondingly small size and thus to desirably limit (or substantially prevent) air flow therethrough.

The peripheral heat seal 15 terminates at the ends of the crease 26, which results from folding one of the free end flaps 28 backwardly (for purposes of illustration). A string 24 is attached to the anterior end of the tampon 12 to assist withdrawal of the article; the string 24 also provides means for extracting the article in the event that it may inadvertently be inhaled by the patient. The neck portion 22 of the sheath serves similar functions, and it may conveniently be taped to the patient's face to thereby ensure its ready accessibility.

Figure 3:
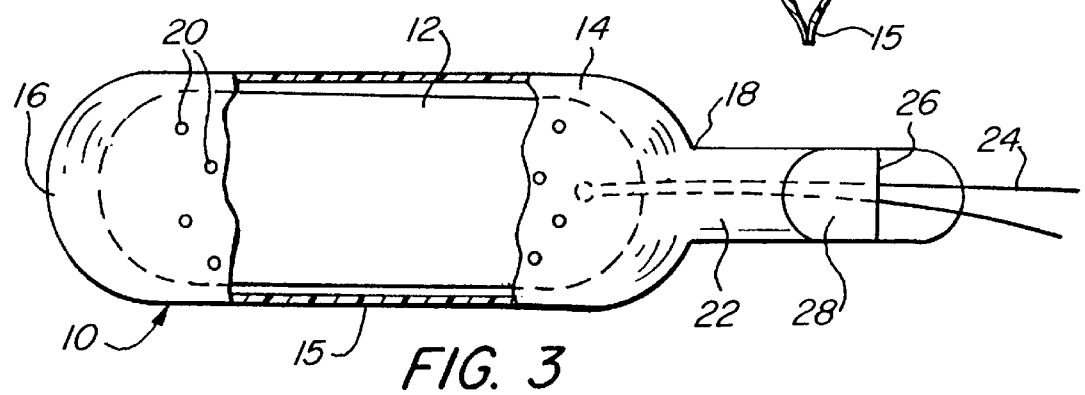
FIG. 3 is a view similar to FIG. 1, showing the tampon component in its expanded state.

As depicted in FIG. 3, the tampon component 12 has been hydrated and expanded to its full dimensions. The expanded sponge substantially fills the space between the sidewalls 13 within the containment portion 14 of the sheath component 10, with neither component exerting a substantial distorting force upon the other.

Figure 4:
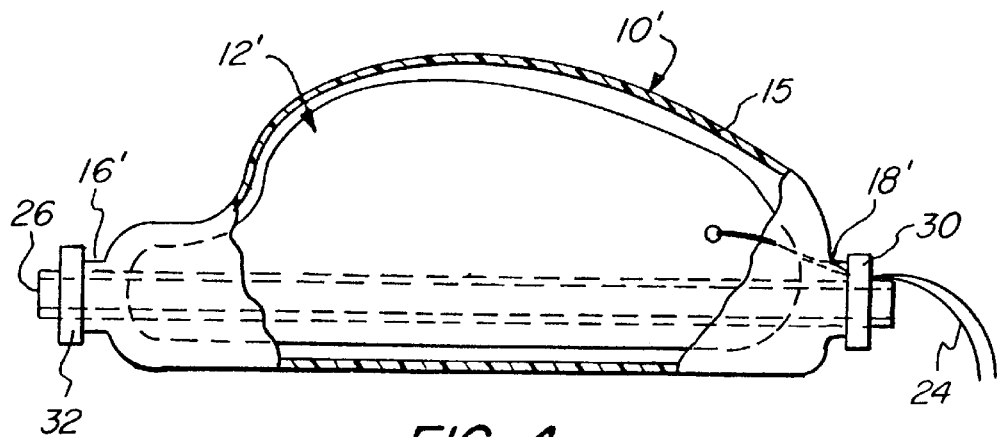
FIG. 4 is a view similar to FIG. 3 but wherein the article is shaped to conform to a nasal cavity and includes an air tube.

The article shown in FIG. 4 is similar to that of the previous figures, but its sheath and tampon components, generally designated respectively by the numerals 10' and 12', are dimensioned and configured to more faithfully conform to the contours of a nasal cavity. In addition however a hollow air tube 26 extends through the sheath 10' and tampon 12', with its opposite end portions protruding from both the posterior end 16' and anterior end 18' of the sheath 10'. At both locations the sheath is formed with a rolled, aperture-defining lip or bead 30, 32, which beads are of such size that the inherent elasticity of the film material causes them to tightly engage circumferentially the protruding end portions of the tube 26, thereby effectively sealing the sheath 10' thereat. In this form of the article, therefore, while both the anterior and the posterior ends of the sheath itself are open, they are closed in the assembly that comprises the article of the invention. A retrieval string 24, attached to the anterior end of the tampon 12', extends along the tube and passes outwardly through the anterior end bead 30.

FIG. 5 shows a variation of the article in which the air tube 26 is disposed exteriorly of the tampon while extending through the sheath, generally designated respectively by the numerals 33 and 34, the sheath 34 having plain, unrolled end portions at 35 and 37. FIG. 6 shows an embodiment in which the sheath, generally designated by the numeral 36, (the tampon not being visible) has a neck portion 38 that is offset from the longitudinal centerline of the body portion 39. The neck portion 38 is of arcuate, or curvilinear, contour so as to enable it to pass more directly, and with less distortion, through the nostril when the article is in place in a nasal cavity.

And finally, FIG. 7 shows a sheath, generally designated 40, fitted with a female element 42 (e.g., a female LUER end) that is temporarily or permanently secured (e.g., by a heat seal) in the open end of the neck portion 44. The female element 42 is constructed to seat and engage the male element 46 (e.g., a male LUER end) of a syringe, generally designated 48, so as to permit facile hydration of the contained sponge (not seen), by liquid from the syringe, with minimal leakage, dripping and waste. The rectilinear neck portion 44 is offset from the longitudinal centerline of the body portion 41, in a relationship similar to that present in the sheath 36 of FIG. 6.

Although the article of the invention may be utilized for packing of other body cavities (e.g., ear canals, sinus and vaginal cavities, etc.), and would of course be constructed (dimensioned and configured) accordingly, it is, once again, particularly well suited for packing of nasal passages. Currently available nasal tampons usually comprise open-cell, biocompatible sponges that are furnished in a compressed state (usually monoaxially or biaxially compressed) and that expand, by contact with a liquid such as blood, mucus, saline solution, etc., to provide a relatively soft and absorbent body. Polyvinyl alcohol, polyvinyl alcohol/aldehyde reaction products, cellulose and cellulose derivatives, polyurethane, and like sponge materials will normally be employed; PVA/formaldehyde sponges will however be preferred in many instances, due especially to the ability of that material to compress from the dry state to an article of stable size and shape.

A significant problem that is entailed in the use of body cavity-packing devices stems from the tendency for the contacting tissues to engage with and adhere to the packing material (due to natural ingrowth or other mechanisms), thereby often making withdrawal not only difficult and painful but also injurious to the contacting tissues and/or healing wounds. In the present article the containing sheath overlies virtually all surfaces of the tampon, thereby preventing substantial tissue attachment and ameliorating the attendant difficulties.

Problems of comparable significance arise moreover from the drying effects of aspiration. Sponges made of resins such as PVA and PVA/formaldehyde are hard and rigid in the dry state; if the sponge is permitted to dry in situ, therefore, extraction will become more difficult and more likely to cause pain and injury. Having at least a closed posterior end (and preferably also at least a substantially closed anterior end), the sheath of the present article protects the tampon against desiccation and thereby helps to maintain it in a soft, pliable condition. Although commonly recommended, rewetting of the sponge prior to removal is often ineffectual or forgotten. After a period of time, moreover, absorbed secretions will tend to coagulate and dry on the packing, thereby compromising its ability to take up any liquid that may be applied for rewetting.

A wide variety of polymeric materials may be employed to produce the sheath of the article, the choice of suitable resins being exemplified by polyethylene, polypropylene, polyurethane, ethylene vinyl acetate, and silicone; certain polymers can be subjected to a gas plasma or corona discharge treatment, to increase their inherent lubricity. The preferred material will be one that can be molded, cast, extruded, or deposited to produce a flat or formed film that will desirably be about 0.5 to 3 mils thick. As will be appreciated, the attributes that the film material is to have will determine the optimal thickness, the primary criteria being comfort to the patient and a degree of suppleness sufficient to permit the film to fold within the cavity without interfering with the intended functions of the article, consistent with adequate strength and integrity. It should be appreciated that the material from which the sheath is fabricated need not be uniform throughout; for example, a heavier gauge material may be used along one side to increase rigidity and thereby provide a stenting feature. The polymer employed will usually have a Shore A Durometer value of 20 to 60, and most desirably 30 to 45. Although any appropriate technique may be utilized to produce the sheath, a particularly suitable alternative to the heat-sealing of superimposed film layers, described in respect of the illustrated embodiments, may be the formation of a seamless body by dip-coating of a mandrel with a liquid form of the polymer or of a polymerizable composition.

Because of inherent elasticity of the polymers that will usually be employed for the sheath, an air tube is readily accommodated as a component of the article. The venting effect that an air tube produces results however in a relatively high volumetric flow rate of turbulent air, which in turn would tend to exacerbate the drying problem in the absence of the protective sheath of which the present article is comprised. Although inherent elasticity of the polymeric film may be relied upon to engage end portions of the tube protruding through simple apertures in the sheath, more effective closure may be achieved by forming rolled beads surrounding the apertures to produce stronger compressive forces upon the tube and hence more secure seals; unrolling of such a bead at the entrance aperture over the tampon may also facilitate its insertion. Withdrawal of the tube from the sheath and tampon will reduce the bulk of the pack and further facilitate its removal.

The prior art makes available a product for nasal packing that is comprised of films laminated to the two opposites sides of a thin sponge body (see for example Cercone et al. U.S. Pat. No. 5,466,231). Unlike the article of the present invention, however, such a laminated product cannot be subjected to compression in two mutually perpendicular directions; doing so would wrinkle and distort the laminated surface films (which are intended to be smooth), and thereby usually render the product unacceptable for surface contact with the body cavity walls. Moreover, sponges that are compressed in only one dimension will typically be trimmed before insertion, for width reduction, thereby diminishing their effectiveness and rendering the packing substantially less desirable. If so desired, however, the tampon of the present article may be removed from the sheath (if provided in assembled condition), such as for trimming, and reinserted prior to introduction into the body cavity.

In addition to the advantages already described, the presence of the sheath on the article of the invention allows the application of water-miscible antibiotic ointments, lubricants (for further reduction of friction, if so desired), and the like, prior to insertion. Because such a coating may be applied to the sheath only it will not interfere with the function of the tampon and will not impede insertion by causing premature expansion. It might be mentioned here that, in the absence of an effective protective sheath, premature expansion can result during the very act of insertion due to the presence at the site of blood or other liquids; the likelihood of encountering difficulty from this effect will be a direct function of the rate of absorption of the sponge material, which will of course desirably be as fast as possible in most instances.

Because the sheath material will itself normally be biocompatible its use enlarges the choice of tampon materials that can suitably be employed. Thus, materials such as cellulose can be utilized without undue concern for medical or surgical compatibility or for the presence of loose fragments of material, etc. Although in most embodiments the sheath will not constrain expansion of the sponge (and vice versa), density variations may be desirable in certain circumstances and may be induced by so configuring the components that expansion of the sponge is restrained by the sheath in selected regions, at which regions higher effective densities will be imparted. Finally, in those instances in which the packing is inserted by use of a mechanical applicator or inserter (typically having a form and construction much like the syringe of FIG. 7, but adapted to contain and discharge a dry tampon), another benefit may result from first introducing the inserter (fully or partially) into the sheath, which may then serve to cover any sharp or abrasive edges or surfaces that may be present. In using such a device, the article of the invention could effectively be assembled in situ; i.e., as the tampon is forced from the applicator it and the sheath (operatively connected to the discharge end of the inserter, in position for receipt of the tampon) would simultaneously be assembled and inserted into the cavity.

The sheath will be usually formed with perforations to permit passage therethrough of liquids from the cavity for absorption by the tampon. (As used herein, the term "perforations" is used to mean any suitable opening, such as an aperture, a straight or crescent-shaped slit, etc., irrespective of the manner by which the opening is produced; the perforations will normally be of such character as to prevent direct contact between the sponge and the existing tissue, developing fibrin, and the like.) Openings will preferably be provided only in the surfaces of the sheath that contact the body cavity walls and lie in direct contact with tissue. Such an arrangement will enable absorption of liquids while, at the same time, blocking the sponge from access to air and thereby keeping it moist and soft. It may be desirable to avoid the presence of perforations in those instances in which, for example, the sheath is coated with an applied substance (e.g., an antibiotic ointment).

Processes for producing suitable sponge materials, and techniques for forming and compressing them, are well known in the art and need not therefore be described here. Reference may be had, for example, to disclosures contained in the patents first identified hereinabove.

Thus, it can be seen that the present invention provides a novel body cavity-packing article comprised of a dry, expansible tampon which is substantially isolated from contact with body tissue and is protected against desiccation. The article of the invention is effective to apply gentle pressure to substantially all parts of the body cavity, including relatively inaccessible openings and recesses thereof; it avoids undue pressure in or overpacking of the cavity, is readily and comfortably inserted, worn, and removed, and is of relatively simple and inexpensive manufacture.

Having thus described the invention, what is claimed is:

1. An article for packing a body cavity, comprising:
a sheath of smooth, supple polymeric film formed to provide a containment portion with a closed posterior end portion and an anterior end entrance aperture spaced therefrom, said anterior end entrance aperture being defined by structure that lies substantially in a transverse plane and has an inherent peripheral dimension that is substantially smaller than the inherent peripheral dimension of any cross sectional element taken along the length of said containment portion between said anterior end entrance aperture and posterior end portion and lying in a plane parallel to said transverse plane; a dry, elongate tampon dimensioned and configured to be loosely disposed entirely within said containment portion of said sheath, and comprised of an absorbent material that is expansible, when wetted, from a dry, stable, compressed state to an expanded state, said dry tampon being compressed to a stable shape and size in two directions that are perpendicular to one another and also to the length dimension of said tampon; and a retrieval element extending from adjacent said anterior end of said sheath and operatively attached for effecting withdrawal of said tampon from a body cavity containing the same, said retrieval element being constructed to extend from the containing body cavity when said article is in place therewith.

2. The article of claim 1 wherein said polymeric film is of a fluid-impermeable material, and wherein said containment portion has perforations along the length thereof between said anterior and posterior ends, said article being thereby adapted for the absorption of liquid substances from the cavity.

3. The article of claim 1 wherein said sheath includes an anterior portion that extends from said anterior end in a direction away from said containment portion.

4. The article of claim 3 wherein said anterior portion is elongate and of reduced transverse cross section, relative to said containment portion, and comprises said retrieval element.

5. The article of claim 1 wherein said containment portion of said sheath is configured to correspond generally to the shape of the body cavity in which said article is to be contained.

6. The article of claim 1 wherein said film has a thickness of about 0.5 to 3 mils and a Shore A Durometer value in the range 20 to 60.

7. The article of claim 6 wherein said film is of a biocompatible polymer selected from the group consisting of latex, silicone, polyolefin, polyurethane, and polyester.

8. The article of claim 1 wherein said compressed tampon has a substantially rectangular cross section, taken in planes transverse to said length dimension.

9. The article of claim 8 wherein said sheath is dimensioned and configured to contain said tampon in its fully expanded state without significant distortion of the expanded tampon by said sheath and without significant distortion of said sheath by said expanded tampon.

10. The article of claim 1 wherein said absorbent material comprises a hydrophilic, open-cell sponge.

11. The article of claim 10 wherein said sponge is of a material selected form the class consisting of cellulose, polyvinyl alcohol, a polyvinyl alcohol/aldehyde condensation product, polyurethane, and combinations thereof.

12. The article of claim 1 further including a hollow tube extending between said anterior and posterior ends of said sheath to provide an airway through said article, said sheath being in sealing engagement with said tube at least at said posterior end to provide closure of said containment portion of said sheath thereat.

13. The article of claim 12 wherein said sheath has an aperture at said posterior end of said containment portion, defined by elastic structure, through which the adjacent end portion of said tube extends in sealing relationship.

14. The article of claim 12 wherein said tube also extends through said tampon.

15. The article of claim 1 wherein said sheath is constructed to effect at least substantial closure of said entrance aperture at said anterior end of said containment portion.

16. The article of claim 15 wherein said peripheral dimension of said entrance aperture structure is not substantially greater than is necessary to permit passage of said compressed tampon therethrough.

17. An article for packing a body cavity, comprising:
a sheath of smooth, supple polymeric film formed to provide a containment portion with a closed posterior end portion and an anterior end entrance aperture spaced therefrom, said anterior end entrance aperture being defined by structure that lies substantially in a transverse plane and has an inherent peripheral dimension that is substantially smaller than the inherent peripheral dimension of any cross sectional element taken along the length of said containment portion between said anterior end entrance aperture and posterior end portion and lying in a plane parallel to said transverse plane, said polymeric film being of a fluid-impermeable material about 0.5 to 3 mils thick and with a Shore A Durometer value of about 20 to 60, and wherein said containment portion has perforations along the length thereof between said anterior end entrance aperture and posterior end portion, said article being thereby adapted for the absorption of liquid substances from the cavity; a dry, elongate tampon dimensioned and configured to be loosely disposed entirely within said containment portion of said sheath, and comprised of an absorbent material that is expansible, when wetted, from a dry, stable, compressed state to an expanded state, said dry tampon being compressed to a stable shape and size in two directions that are perpendicular to one another and also to the length dimension of said tampon, said peripheral dimension of said anterior end entrance aperture structure being not substantially greater than is necessary to permit passage of said compressed tampon therethrough.

18. The article of claim 17 wherein said film is of a biocompatible polymer selected from the group consisting of latex, silicone resin, polyolefin, polyurethane, and polyester.

19. An article for packing a body cavity, comprising:
a sheath of smooth, supple polymeric film formed to provide a containment portion with a closed posterior end portion and an anterior end entrance aperture spaced therefrom, said anterior end entrance aperture being defined by structure that lies substantially in a transverse plane and has an inherent peripheral dimension that is substantially smaller than the inherent peripheral dimension of any cross sectional element taken along the length of said containment portion between said anterior end entrance aperture and posterior end portion and lying in a plane parallel to said transverse plane; a dry, elongate tampon dimensioned and configured to be loosely disposed entirely within said containment portion of said sheath, and comprised of an absorbent material that is expansible, when wetted, from a dry, stable, compressed state to an expanded state, said dry tampon being compressed to a stable shape and size in two directions that are perpendicular to one another and also to the length dimension of said tampon; and a hollow tube extending between said anterior end entrance aperture and posterior end portion of said sheath to provide an airway through said article, said sheath being in sealing engagement with said tube at least at said posterior end portion to provide closure of said containment portion of said sheath thereat.

20. The article of claim 19 wherein said sheath has an aperture at said posterior end of said containment portion, defined by elastic structure, through which the adjacent end portion of said tube extends in sealing relationship.

21. The article of claim 19 wherein said sheath is constructed to effect at least substantial closure of said entrance aperture at said anterior end of said containment portion.

* * * * *